(12) United States Patent
Dang

(10) Patent No.: US 6,362,340 B1
(45) Date of Patent: Mar. 26, 2002

(54) METHOD FOR PREPARING 4-HYDROQUINOLINES AND/OR TAUTOMERIC COMPOUNDS

(75) Inventor: Tuan-Phat Dang, Lyons (FR)

(73) Assignee: Rhodia Chimie, Boulogne-Billancourt (FR)

(*) Notice: Subject to any disclaimer, the term of this patent is extended or adjusted under 35 U.S.C. 154(b) by 0 days.

(21) Appl. No.: 09/856,810

(22) PCT Filed: Dec. 1, 1999

(86) PCT No.: PCT/FR99/02985

§ 371 Date: May 25, 2001

§ 102(e) Date: May 25, 2001

(87) PCT Pub. No.: WO00/32576

PCT Pub. Date: Jun. 8, 2000

(30) Foreign Application Priority Data

Dec. 1, 1998 (FR) .............................. 98/15126

(51) Int. Cl.⁷ ...................... C07D 215/22; C07D 215/56
(52) U.S. Cl. ...................................................... 546/153
(58) Field of Search ........................................ 546/153

(56) References Cited

FOREIGN PATENT DOCUMENTS

| EP | 748799 | 12/1996 |
|---|---|---|
| WO | 98/33774 | 8/1998 |

*Primary Examiner*—Zinna Northington Davis

(57) ABSTRACT

The invention concerns a method for preparing 4-hydroquinolines and/or tautomeric compounds. More particularly, the invention concerns 5,7-dichloro-4-quinolines and/or its tautomeric compounds. The method is characterized in that it consists in heating a 4-hydroquinolinecarboxylic acid, its derivatives or precursors, at a temperature not more than 200° C. in the presence of a base.

22 Claims, No Drawings

METHOD FOR PREPARING 4-HYDROQUINOLINES AND/OR TAUTOMERIC COMPOUNDS

This application is an application under 35 U.S.C. Section 371 of International Application Number PCT/FR99/02985 filed on Dec. 1, 1999.

The present invention relates to a process for preparing 4-hydroxyquinolines and/or their tautomeric forms. More particularly, the invention relates to 5,7-dichloro-4-hydroxyquinoline and/or its tautomeric forms.

5,7-dichloro-4-hydroxyquinoline (DCHQ) is an intermediate used in the plant protection field.

The industrial scale preparation of such a product is a problem, and existing processes are in need of refining.

C. C. Price et al. (Organic Synthesis 3, p. 272) disclose the preparation of 4-hydroxyquinolines using a process consisting of decarboxylation of 4-hydroxy-3-quinolinecarboxylic acids that have been obtained by alkaline or acid hydrolysis of the corresponding esters. However, decarboxylation is carried out at a high temperature of more than 230° C.

U.S. Pat. No. 5,731,440 proposes improving that process by carrying out the decarboxylation step at a lower temperature in the range 120° C. to 165° C., but uses a strong acid medium such as sulphuric acid, phosphoric acid or hydrochloric acid. The disadvantage of that process is that the medium is highly corrosive because of the presence of a strong acid.

The Applicant has discovered an improved hydroxyquinoline preparation process.

The process of the invention is characterized in that a 4-hydroxyquinolinecarboxylic acid, a derivative or precursor thereof, is heated to a temperature of at most 200° C. in the presence of a base.

It has unexpectedly been discovered that it is possible to carry out decarboxylation of 4-hydroxyquinolinecarboxylic acids and esters thereof at a low temperature, advantageously in the range 90° C. to 160° C., in good reaction yields. This is of enormous advantage from an industrial viewpoint.

The process of the invention uses a quinolinic compound.

The term "quinolinic compound" means a heterocyclic compound comprising a quinoline moiety. This term is also used for naphthpyridine type compounds that are also included in the scope of the process of the invention.

The heterocycle of the quinolinic compound carries at least one hydroxyl group in the 4-position and a functional group in the position α to the hydroxyl group. Other substituents can also be present in particular in the 5- and/or 7-position.

Regarding the nature of the functional group that is shown in formula (I) below by the symbol Y, this is a carboxylic group (COOH), a precursor group (nitrile) or a derivative group (ester or amide).

The starting quinolinic compound of the invention can be represented by the following general formula:

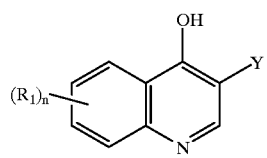

in which formula (I):

R$_1$, which may be identical or different, represents:
a linear or branched alkyl group containing 1 to 12 carbon atoms, preferably 1 to 4 carbon atoms, such as methyl, ethyl, propyl, isopropyl, butyl, isobutyl, sec-butyl, tert-butyl;
a linear or branched alkyl group carrying one or more halogen atoms, containing 1 to 6 carbon atoms, preferably 1 to 4 carbon atoms, such as methyl, ethyl, propyl, isopropyl, butyl, isobutyl, sec-butyl, tert-butyl;
a linear or branched alkenyl group containing 2 to 12 carbon atoms, preferably 2 to 4 carbon atoms, such as vinyl or allyl,
a cyclohexyl, phenyl or benzyl group;
a linear or branched alkoxy or thioether group containing 1 to 6 carbon atoms, preferably 1 to 4 carbon atoms, such as a methoxy, ethoxy, propoxy, isopropoxy or butoxy radical;
an acyl group containing 2 to 6 carbon atoms;
a nitro group;
an amino group, optionally substituted by alkyl groups containing 1 to 6 carbon atoms;
a halogen atom, preferably a chlorine or bromine atom;
a trifluoromethyl group;
an alkenylene group containing 3 or 4 carbon atoms that can form a ring with the carbon atoms adjacent to the phenyl ring;

Y represents one of the following groups:
a CN group;
a COOR$_2$ group;
a CONR$_3$R$_4$ group;
in which groups R$_2$, R$_3$ or R$_4$, which may be identical or different, represent a hydrogen atom or an alkyl, cyclohexyl, phenyl or benzyl group;

n is a number in the range 1 to 4, preferably 1 or 2.

Particularly suitable substituents in the 5- and/or 7-position are halogen atoms such as fluorine, chlorine, bromine, iodine or a —CF$_3$ type group.

Preferred non-limiting illustrative examples from the list of substituents are the chlorine atom, methyl radical and methoxy radical.

The nature of R$_2$, R$_3$ and R$_4$ is not critical provided that the carboxylate group is eliminated. For reasons of economy, it is usually a linear or branched alkyl group containing 1 to 6 carbon atoms, preferably 1 to 4 carbon atoms, but it is possible to use other groups, for example cyclohexyl, phenyl or benzyl groups, or any other group.

More particular compounds with formula (I) for use in the process of the invention that can be cited are 4-hydroxy-5,7-dichloroquinoline-3-carboxylic acid, and methyl or ethyl 4-hydroxy-5,7-dichloroquinoline-3-carboxylate.

The starting quinolinic compounds with formula (I) are known products that can in particular be obtained by reacting substituted anilines with alkyl alkoxymethylenemalonates (cf. C. C. Price et al., Organic Synthesis 3, p. 272).

It should be noted that the invention is applicable to quinolinic compounds with formula (I) and also to tautomeric forms that can be represented by formula (II):

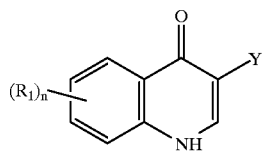
(II)

in which formula (II), $R_1$, Y and n have the meanings given above for formula (I).

In accordance with the process of the invention, the quinolinic compound is decarboxylated in the presence of a base.

A mineral or organic base can be used in the process of the invention.

Preferably, a sufficiently strong base is selected, i.e., a base with an associated acid the pKa of which is more than 5 or close to 5: the pKa is defined as the cologarithm of the dissociation constant of the acid, in an aqueous medium, at 25° C.

Particularly suitable bases for carrying out the process of the invention that can be cited are alkaline bases derived from alkali metals or alkaline-earth metals.

The term "alkali metals" as used in the present text means elements from column 1A of the periodic table, preferably alkali metals such as lithium, sodium, potassium, rubidium and caesium.

The term "alkaline-earth metal" as used in the present text means elements from column 2A of the periodic table, preferably alkaline-earth metals such as beryllium, magnesium, calcium, strontium and barium.

For a definition of the elements, reference should be made to the periodic table published in the "Bulletin de la Société Chimique de France", N° 1, (1966).

The process of the invention preferably employs an alkali metal hydroxide, preferably potassium hydroxide or sodium hydroxide, or an alkali metal bicarbonate or carbonate, preferably potassium or sodium bicarbonate or carbonate.

It is also possible to use a quaternary ammonium hydroxide.

Examples of quaternary ammonium hydroxides that are preferably used are tetraalkylammonium or trialkylbenzylammonium hydroxides wherein the alkyl radicals, which may be identical or different, represent a linear or branched alkyl chain containing 1 to 12 carbon atoms, preferably 1 to 6 carbon atoms.

Preferably, tetramethylammonium hydroxide, tetraethylammonium hydroxide or tetrabutylammonium hydroxide are used.

It is also possible to use trialkylbenzylammonium hydroxides, in particular trimethylbenzylammonium hydroxide.

The process of the invention can also employ monofunctional or bifunctional primary, secondary or tertiary aliphatic, carbocyclic or heterocyclic, aromatic or non aromatic amines.

More specific examples that can be mentioned are tri-n-butylamine, di-n-butylamine, hexamethylenediamine, cyclohexylamine, N-methylpyrrolidine, 4-dimethylaminopyridine, morpholine, quinoline, pyridine, 3-picoline and 5-picoline.

From an economic and practical viewpoint, the base that is selected is preferably potassium or sodium hydroxide.

The base is advantageously used in the form of an aqueous solution.

The concentration of the basic solution is preferably in the range 2% to 45% by weight, more preferably in the range 5% to 30%.

The quantity of based used, expressed as the mole ratio between the number of moles of base (or equivalents of base) and the number of moles of quinolinic compound, is preferably in the range 1 to 6, more preferably in the range 1.5 to 3.5.

The decarboxylation reaction carried out in the process of the invention is preferably carried out in the presence of water, which can be in the liquid and/or vapour form.

The quantity of quinolinic compound used preferably represents 2% to 50%, more preferably 5% to 35% by weight of the weight of the water.

Preferably, the water is supplied by the basic solution.

The process of the invention can be implemented in a number of ways.

In a first variation, decarboxylation is carried out by heating the reaction mixture including the quinolinic compound, the base and water.

In a second variation, the quinolinic compound and the base are mixed in aqueous solution, the water is evaporated off then the decarboxylation reaction is effected by heating in a completely solid medium.

Finally, in a third variation of the process of the invention, an organic solvent that may or may not be miscible with water is added to a reaction medium including the quinolinic compound, base, and water.

The organic solvent does not have to dissolve the quinolinic compound.

Preferably, an organic solvent is selected that is not miscible with water and has a high boiling point.

A preferred solvent for this type of reaction is a eutectic mixture of biphenyl oxide and biphenyl sold under the trade names of THERMINOL VP1, DOWTHERM or GILOTHERM DO. When used, the decarboxylation temperature is advantageously selected so as to be in the preferred temperature zone.

It is also possible to use other solvents such as triphenylmethane, sulpholane, benzylbenzene, 1,4-dibenzylbenzene, a silicone oil or petroleum cuts with a high boiling point of more than the selected reaction temperature.

Organic solvents such as dimethylformamide or N,N'-diacetamide are also suitable.

An alcohol type solvent is also suitable, more particularly propanol, isopropanol or n-butanol.

The concentration of quinolinic compound in the organic solvent is such that the weight ratio between the organic solvent and the quinolinic compound is preferably in the range 1 to 30, more preferably in the range 1 to 10.

If the base used is liquid, for example an amine, it is also possible to implement a further variation which consists of carrying out decarboxylation by heating the reaction mixture comprising the quinolinic compound and a base, in the absence of water.

Thus, depending on the implementations of the invention, the medium can be liquid, solid or two-phase (liquid/liquid or liquid/solid) or even three-phase (liquid/liquid/solid). Thus the choice of reactor will be adapted as a consequence.

The reaction is carried out under autogenous pressure.

Regarding the decarboxylation operation proper, it is carried out by heating the reaction medium. The decarboxylation temperature is at most 200° C., preferably in the range 90° C. to 190° C., and more preferably in the range 95° C. to 180° C.

The heating period must be sufficient for the reaction to be completed to a sufficient degree.

It should be noted that the process is of particular importance when using a quinolinic compound in the form of an ester, as because of the presence of the base, ester hydrolysis occurs during the decarboxylation step, simultaneously and/or successively.

At the end of the operation, depending on the quantity of base used, a product is obtained in the free (acid) form or salt form that essentially comprises the desired quinolinic compound (B) in equilibrium with its tautomeric form (A), with the following formulae:

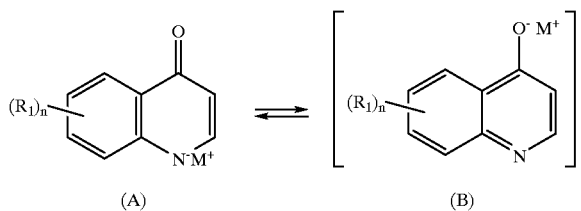

where $R_1$ and n have the meanings given above and M represents a hydrogen atom or the cation of the base introduced initially. This cation is preferably an alkali metal if the base used initially is an alkali metal hydroxide, as indicated above.

At the end of the reaction, the reaction medium is treated conventionally.

Thus, when the organic phase is present and when the base is used in excess, the product obtained is in the form of the salt in the aqueous phase which is separated from the organic phase, for example by decanting.

When the base is in excess, acid treatment is carried out to recover the desired free product in the form of a precipitate.

To this end, an acid is added, preferably hydrochloric acid, sulphuric acid or phosphoric acid, in a quantity such that the 4-hydroxyquinoline produced is in the free form.

The concentration of the starting acid is anywhere in the range 10% to 90% by weight of acid, but preferably, a dilute acid solution is used, preferably 20% to 50% by weight.

The precipitate is separated using conventional solid-liquid separation techniques, preferably by filtering.

Washing the precipitate to eliminate traces of organic liquid may be desirable. To this end, water or a solvent with a low boiling point can be used, for example less than 150° C., preferably in the range 60° C. to 120° C. Particular examples of eminently suitable solvents are: o-dichlorobenzene, methylcyclohexane, benzene, toluene, chlorobenzene, methanol and ethanol.

The decarboxylated product is obtained in a very high yield.

When the base is not used in excess, acid does not need to be added. The free quinolinic compound is obtained directly in the form of a precipitate which only needs separation, for example by filtering.

The filtrate which contains the base is optionally recycled to other decarboxylation operations.

The invention is particularly suitable for the preparation of a 4-hydroxy-7-halogenoquinolines, preferably 4-hydroxy-7-chloroquinoline and its isomer, or a 4-hydroxy-5-halogenoquinoline, preferably 4-hydroxy-5-chloroquinoline. It is eminently suitable for preparing 5,7-dichloro-4-hydroxyquinoline.

Examples will now be given which illustrate the invention without in any way limiting its scope.

In the examples, the percentages are given by weight.

The abbreviations have the following meanings:

DCHQ=5,7-dichloro-4-hydroxyquinoline;

ODCQA=4-hydroxy-5,7-dichloroquinoline-3-carboxylic acid;

The degree of transformation (TT) corresponds to the ratio between the number of moles of substrate transformed and the number of moles of substrate engaged;

The yield (RR) corresponds to the ratio between the number of moles of product formed and the number of moles of substrate engaged.

EXAMPLE 1

1.55 g (6 mmoles) of 4-hydroxy-5,7-dichloroquinoline-3-carboxylic acid (ODCQA) and 5.6 g of an aqueous 12% potassium hydroxide solution (12 mmoles of KOH) were charged into an autoclave, then it was stirred at 150° C.

After reacting for 5 hours, high performance liquid chromatographic analysis was carried out:

degree of transformation (TT) of ODCQA>99%;

DCHQ yield=99%.

EXAMPLES 2 TO 13

The same procedure as that used in Example 1 was used, changing certain parameters; in particular, an organic solvent was used in Examples 7 to 10, namely therminol VP1, a eutectic mixture of biphenyl and biphenyl oxide.

The results obtained are shown in Table (I).

TABLE (I)

| Ref. Ex. | KOH/ODCQA mole ratio | [KOH] % | Solvent | T° C. | Time h | TT ODCQA % | RR DCHQ % |
|---|---|---|---|---|---|---|---|
| 2 | 1.8 | 25 | None | 95 | 63 | 37 | 36 |
| 3 | 2 | 25 | None | 95 | 63 | 43 | 51 |
| 4 | 2.2 | 25 | None | 95 | 63 | 49 | 48 |
| 5 | 4 | 30 | None | 95 | 15 | — | 11 |
| 6 | 4 | 25 | None | 105 | 15 | 8 | 9 |
| 7 | 1.5 | 25 | Therminol VP1 | 110 | 15 | 44 | 30 |
| 8 | 2 | 25 | Therminol VP1 | 110 | 15 | 62 | 57 |
| 9 | 2.5 | 25 | Therminol VP1 | 110 | 15 | 74 | 70 |
| 10 | 2 | 25 | Therminol VP1 | 120 | 15 | 89 | 63 |

TABLE (I)-continued

| Ref. Ex. | KOH/ ODCQA mole ratio | [KOH] % | Solvent | T° C. | Time h | TT ODCQA % | RR DCHQ % |
|---|---|---|---|---|---|---|---|
| 11 | 2.5 | 12 | None | 150 | 5 | >99 | 93 |
| 12 | 3 | 12 | None | 150 | 5 | 98 | 67 |
| 13 | 4.5 | 12 | None | 150 | 5 | 56 | 56 |

EXAMPLE 14

The procedure of the above examples was followed, operating in the absence of an organic solvent, with a KOH/ODCQA mole ratio of 2: the water present was supplied by the KOH solution.

The results obtained are shown in the following table:

TABLE (II)

| Ref. Ex. | KOH/ ODCQA mole ratio | [KOH] mol/kg of reaction medium | Solvent | T° C. | Time h | TT ODCQA % | RR DCHQ % |
|---|---|---|---|---|---|---|---|
| 14 | 2 | 1.35 | None | 140 | 5 | 99.4 | 97 |

EXAMPLE 15

1.55 g (6 mmoles) of 4-hydroxy-5,7-dichloroquinoline-3-carboxylic acid (ODCQA) and 9.8 g of an aqueous 12% potassium hydroxide solution (21 mmoles of KOH) were charged into an autoclave, then it was stirred at 150° C.

After reacting for 5 hours, high performance liquid chromatographic analysis was carried out on a sample that had been removed.

The following results were obtained:
degree of transformation (TT) of ODCQA=77%;
DCHQ yield=77%.

11.56 g of an aqueous 10% sulphuric acid solution (11.9 mmoles) was added to the crude mixture (10.45 g, corresponding to 92% of the total initial mass) remaining after removing the sample for analysis.

The reaction mixture was stirred at 70° C. for 50 min, and the precipitate obtained was washed with water then dried under reduced pressure (10 mm of mercury) at 70° C.

1.24 g of product was obtained.

High performance liquid chromatography of this product showed that it contained 75% of DCHQ and 25% of ODCQA.

EXAMPLE 16

1.72 g (6 mmoles) of ethyl 4-hydroxy-5,7-dichloroquinoline-3-carboxylate (ODCQE), 2.69 g of an aqueous 25% potassium hydroxide solution (12 mmoles of KOH) and 6.45 g of Therminol VP1 were charged into an autoclave and heated to 150° C. with stirring.

After reacting for 15 hours, high performance liquid chromatography analysis was carried out with a slightly acidic eluent:
degree of transformation (TT) of ODCQE>99%;
degree of transformation (TT) of ODCQA>99%;
DCHQ yield=86%.

EXAMPLES 17 TO 22

The same procedure as that used for Example 16 was used, changing certain parameters.

The results obtained are shown in Table (III).

TABLE (III)

| Ref. Ex. | KOH/ ODCQA mole ratio | [KOH] % | Solvent | T° C. | Time h | TT ODCQE % | TT ODCQA % | RR DCHQ % |
|---|---|---|---|---|---|---|---|---|
| 17 | 2 | 25 | Therminol VP1 | 95 | 63 | 100 | 61 | 55 |
| 18 | 2 | 25 | Therminol VP1 | 110 | 15 | 100 | 43 | 39 |
| 19 | 2.5 | 25 | Therminol VP1 | 110 | 15 | 100 | 71 | 65 |
| 20 | 1.5 | 25 | Therminol VP1 | 110 | 15 | 100 | 39 | 26 |
| 21 | 2 | 25 | DMAC | 120 | 15 | 100 | 51 | 21 |
| 22 | 2.5 | 25 | Therminol VP1 | 120 | 15 | 100 | 95 | 84 |

EXAMPLE 23 a—Preparation of ethyl 4-hydroxy-5,7-dichloroquinoline-3-carboxylate 266 ml of Therminol VP1, 56.8 g (0.263 mole) of ethyl ethoxymethylenemalonate and 41.3 g (0.255 mole) of 3,5-dichloroaniline were introduced into a stirred reactor provided with a distillation column.

The mixture was heated from ambient temperature to 248° C. over 3 h 30 minutes, then maintained at 248° C. for 3 h; the ethanol formed was distilled off as it was formed.

b—Hydrolysis—Decarboxylation of the ethyl 4-hydroxy-5,7-dichloroquinoline-3-carboxylate obtained The temperature of the reaction mixture obtained above was reduced to 95° C. and 142.3 g of aqueous 25% potassium hydroxide solution (0.638 moles) was added.

It was heated to 95° C.–100° C. for 9 hours then 28.6 g of aqueous 25% potassium hydroxide solution (0.128 moles) was added.

It was decanted at 85° C. for 2 hours than the aqueous potassium hydroxide phase was separated from the Therminol VP1 phase.

This aqueous phase was acidified with 412 g of an aqueous 10.5% sulphuric acid solution (0.437 moles).

The precipitate obtained was filtered, washed with water and dried.

48.8 g of a product containing 66% of ODCQA and 33% of the decarboxylated product DCHQ were obtained.

EXAMPLES 24 TO 26

In the following examples, sodium hydroxide was used in place of potassium hydroxide.

The conditions used and results obtained are shown in Table (IV).

TABLE (IV)

| Ref. Ex. | NaOH/ODCQA mole ratio | [NaOH] mol/kg of reaction medium | Solvent | T° C. | Time h | TT ODCQA % | RR DCHQ % |
|---|---|---|---|---|---|---|---|
| 24 | 1.19 | 0.7 | None | 140 | 7 | 85.5 | 85.5 |
| 25 | 1.60 | 1.05 | None | 140 | 7 | 90 | 89.8 |
| 26 | 2.05 | 1.35 | None | 140 | 7 | 90 | 89.3 |

EXAMPLE 27

The following were charged into a 1.5 liter LIST discotherm B® reactor:

1 liter of water;

50.4 g of sodium bicarbonate (0.6 moles);

154.8 g of ODCQA (0.6 moles).

It was stirred at 30 rpm.

A suspension was obtained and gas evolution was observed.

The autoclave was closed and heated for 45 min to 120° C.: the pressure was 4.87 bars.

It was degassed to 3 bars.

It was re-sealed and heated for 2 hours 15 minutes to 150° C., decompressing from time to time (twice).

When the reaction was complete, the pressure was 686 bars.

It was cooled and the pressure was returned to atmospheric pressure.

A suspension was obtained which was diluted with 1 liter of water.

1920 g of suspension was recovered.

The suspension was filtered and 315 g of moist cake was obtained along with 1698 g of mother liquor.

After drying the moist cake, 138.6 g of dry product with the following composition was obtained:

ODCG=98%;

ODCQA=0.83%

The base initially introduced was present in the mother liquor which could thus be recycled to a new decarboxylation step to prevent the discharge of effluents.

What is claimed is:

1. A process for the preparation of a 4-hydroxyquinoline compound, or its tautomeric form, from a starting compound having the following formula:

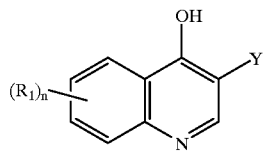

(I)

wherein:

$R_1$, which is identical or different, represents a linear or branched alkyl group containing 1 to 12 carbon atoms, a linear or branched alkyl group containing 1 to 6 carbon atoms, carrying one or more halogen atoms, a linear or branched alkenyl group containing 2 to 12 carbon atoms, a cyclohexyl group, a phenyl group, a benzyl group, a linear or branched alkoxy or group containing 1 to 6 carbon atoms, a linear or branched thioether group containing 1 to 6 carbon atoms, an acyl group containing 2 to 6 carbon atoms, a nitro group, an amino group, optionally substituted by alkyl groups containing 1 to 6 carbon atoms, a halogen atom, a trifluoromethyl group, or an alkenylene group containing 3 or 4 carbon atoms, optionally forming a ring with a carbon atom adjacent to a phenyl ring;

Y represents a CN group, a $COOR_2$ group, or a $CONR_3R_4$ group, wherein groups $R_2$, $R_3$ or $R_4$, which are identical or different, represent a hydrogen atom, an alkyl group, a cyclohexyl group, a phenyl group, or a benzyl group;

n is a number in the range 1 to 4, said process comprising the steps of:

a) heating said starting compound to a temperature of at most 200° C. in the presence of a base, and b) recovering the compound obtained in step a).

2. A process according to claim 1, wherein groups $R_1$, which are identical or different, represent a chlorine atom, a methyl group, or a methoxy group.

3. A process according to claim 1, wherein groups $R_2$, $R_3$ and $R_4$, which are identical or different, represent a hydrogen atom or an alkyl group containing 1 to 6 carbon atoms.

4. A process according to claim 1, wherein the starting compound with formula (I) is in its tautomeric form (II):

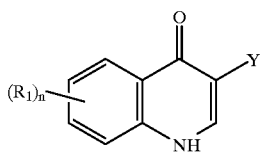

(II)

wherein $R_1$, which is identical or different, represents a linear or branched alkyl group containing 1 to 12 carbon atoms, a linear or branched alkyl group containing 1 to 6 carbon atoms, carrying one or more halogen atoms, a linear or branched alkenyl group containing 2 to 12 carbon atoms, a cyclohexyl group, a phenyl group, a benzyl group, a linear or branched alkoxy or group containing 1 to 6 carbon atoms, a linear or branched thioether group containing 1 to 6 carbon atoms, an acyl group containing 2 to 6 carbon atoms, a nitro group, an amino group, optionally substituted by alkyl groups containing 1 to 6 carbon atoms, a halogen atom, a trifluoromethyl group, or an alkenylene group containing 3 or 4 carbon atoms, optionally forming a ring with a carbon atom adjacent to a phenyl ring;

Y represents a CN group, a $COOR_2$ group, or a $CONR_3R_4$ group, wherein groups $R_2$, $R_3$ or $R_4$, which are identical or different, represent a hydrogen atom, an alkyl group, a cyclohexyl group, a phenyl group, or a benzyl group;

n is a number in the range 1 to 4.

5. A process according to claim 1, wherein the starting compound is 4-hydroxy-7-chloroquinoline-3-carboxylic acid, 4-hydroxy-5-chloroquinoline-3-carboxylic acid, or 4-hydroxy-5,7-dichloroquinoline-3-carboxylic acid.

6. A process according to claim 1, wherein the starting compound is 4-hydroxy-5,7-dichloroquinoline-3-carboxylic acid, methyl 4-hydroxy-5,7-dichloroquinoline-3-carboxylate, or ethyl 4-hydroxy-5,7-dichloroquinoline-3-carboxylate.

7. A process according to claim 1, wherein the base is an alkaline base.

8. A process according to claim 7, wherein the base is an alkali metal hydroxide, an alkali metal bicarbonate or an alkali metal carbonate.

9. A process according to claim 7, wherein the mole ratio between the number of moles of base, or equivalents of base, and the number of moles of the starting compound is in the range 1 to 6.

10. A process according to claim 7, wherein the mole ratio between the number of moles of base, or equivalents of base, and the number of moles of the starting compound is in the range 1.5 to 3.5.

11. A process according to claim 1, wherein step a) essentially consists in a decarboxylation reaction carried out in the presence of water in liquid or vapor form.

12. A process according to claim 11, wherein the quantity of starting compound represents 2% to 50% by weight of the water.

13. A process according to claim 11, wherein the quantity of starting compound represents 5% to 35% by weight of the water.

14. A process according to claim 1, wherein in step a) the temperature is between 90° C. and 190° C.

15. A process according to claim 1, wherein in step a) the temperature is between 95° C. and 180° C.

16. A process according to claim 11, wherein the decarboxylation reaction is carried out by heating a reaction mixture comprising the starting compound, the base and water.

17. A process according to claim 11, further comprising, before step a), the steps of mixing in an aqueous solution the starting compound and the base, and evaporating off the water, the decarboxylation being carried out by heating in a solely solid medium.

18. A process according claim 11, wherein the decarboxylation reaction is carried out in the presence of an organic solvent.

19. A process according to claim 18, wherein the organic solvent is a paraffin oil, an eutectic mixture of biphenyl oxide and biphenyl, a triphenylmethane, a sulpholane, a benzylbenzene, a 1,4-dibenzylbenzene, a silicone oil, a petroleum cut with a high boiling point, a dimethylformamide, a N,N'-diacetamide, or an alcohol.

20. A process according to claim 18, wherein the concentration of the starting compound in the organic solvent is such that the organic solvent and the starting compound present a weight ratio solvent/starting compound of between 1 and 10.

21. A process according to claim 18, wherein the concentration of the starting compound in the organic solvent is such that the organic solvent and the starting compound present a weight ratio solvent/starting compound of between 1 and 10.

22. A process according to claim 1, wherein recovering in step b) is carried out by a solid/liquid separation, optionally after an acidic treatment.

* * * * *